United States Patent [19]
Johansen

[11] Patent Number: 5,620,004
[45] Date of Patent: Apr. 15, 1997

[54] AIRWAY INDICATOR DEVICE

[76] Inventor: Aaron Johansen, 206 E. 95th St., New York, N.Y. 10128

[21] Appl. No.: 546,669
[22] Filed: Oct. 23, 1995
[51] Int. Cl.⁶ .............................. A61B 5/07; A61M 29/00
[52] U.S. Cl. .......................... 128/716; 128/773; 128/725; 128/730; 128/721; 604/100
[58] Field of Search ........................ 128/202.22, 207.15, 128/716, 721, 725–728, 730, 670, 773, 911; 604/100

[56] References Cited

U.S. PATENT DOCUMENTS

| 5,295,489 | 3/1994 | Bell et al. | 128/736 |
| 5,487,731 | 1/1996 | Denton | 604/100 |

Primary Examiner—Angela D. Sykes
Assistant Examiner—Stephen Huang
Attorney, Agent, or Firm—Michael G. Petit

[57] ABSTRACT

An indicator device for verifying the correct placement of an endotracheal tube within an intubated patient's airway and for detecting the presence of a collapsed lung in an intubated patient. The device has an open proximal end and open distal end and an air conducting lumen therebetween. The distal end is attached to the non-invasive end of an endotracheal tube. The proximal end is attached to a ventilating apparatus or "ambubug." A vibrating element mounted within the device produces an audible vibration either actively in response to an electrical driver, or passively in response to air flowing through the device. As the ambubag is squeezed, air is forced through the air conducting lumen and into the intubated patient's airway. An audible sound produced by the vibrating element is mechanically coupled into the air conducting lumen and conducted through the patient's airway. A stethoscope placed upon the chest adjacent to the lungs of the intubated patient readily detects the audible sound thereby verifying airway patency and the correct positioning of the tube within the patients airway. Alternatively, an electrical driver may be used for controlling the vibrating element. The device can be used to detect a hemothorax or a pneumothorax in an intubated patient by measuring and comparing the attenuation or amplification of the audible sound transmitted to various positions on the chest. A preferred embodiment of the device includes a syringe-receiving port for attaching an aspirating syringe to the air conducting lumen. The syringe provides means for additional confirmation of a patent airway and/or for the delivery of medicament to the intubated patient.

6 Claims, 2 Drawing Sheets

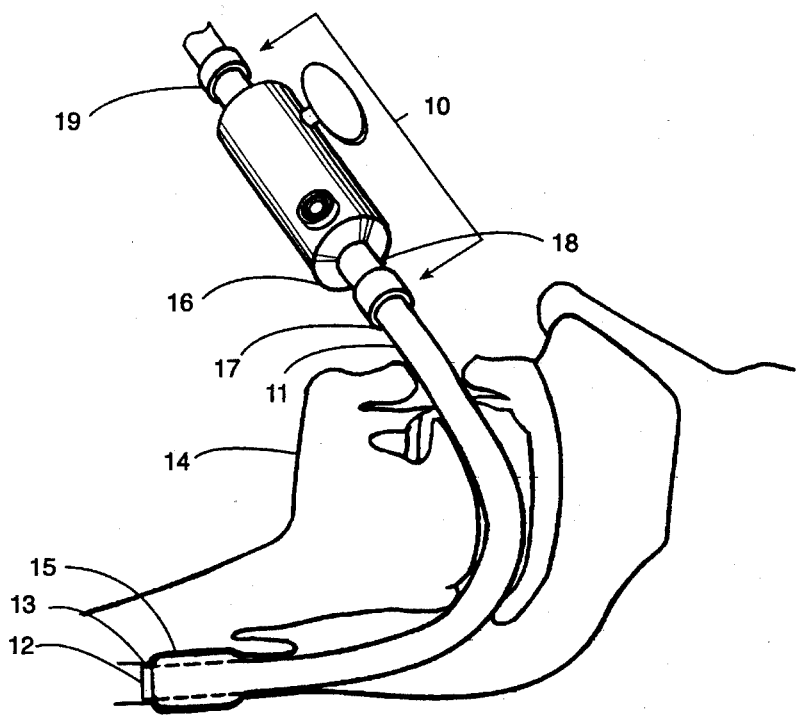
Figure 1
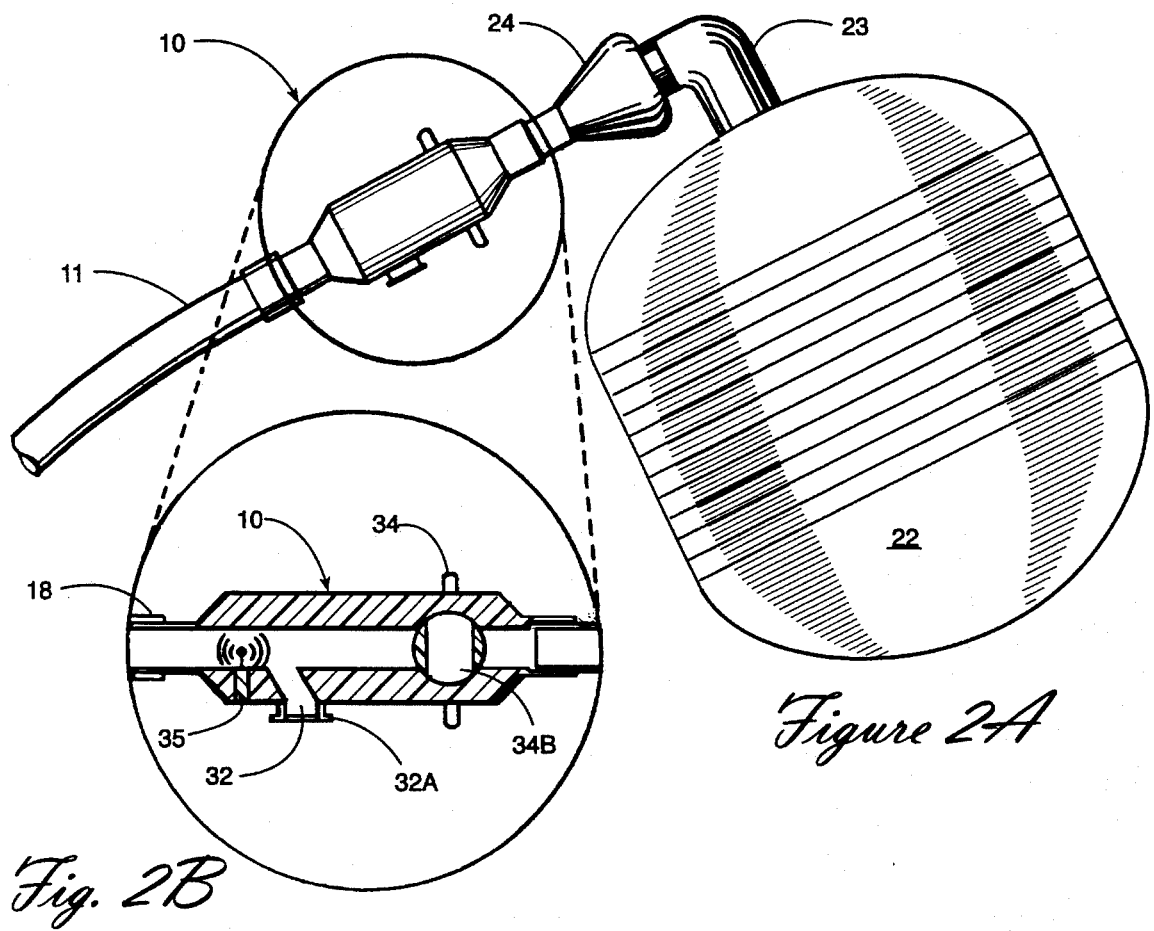
Figure 2A
Fig. 2B

AIRWAY INDICATOR DEVICE

BACKGROUND OF THE INVENTION

1. Field of the Invention

This invention relates to a device for verifying the position of an endotracheal tube within the airway of an animal and the condition the lungs of an intubated animal, particularly a human.

2. Prior Art

Endotracheal intubation is essential for controlled, proactive airway management. Intubation enables the establishment and maintenance of patency while providing immediate access to the airway and the ability to regulate ventilation and deliver drugs. Further, intubation enables the health care provider to gain time for the resolution of any acute, reversible, life threatening condition by supporting vital functions that are severely compromised or at risk of failure. The disadvantage of intubation is that specialized equipment must be available, as well as a practitioner having specialized training. Since intubation is an invasive procedure, contamination, infection and related complications are an ever present danger.

Since intubation is by no means a facile procedure, a number of approaches have been developed to confirm or verify the position of the endotracheal tube within the airway of the patient. Direct visualization of the distal tip of the endotracheal tube as it passes between the vocal cords is the method most commonly used to verify correct placement of the tube. Visualization can be achieved by means of a steerable endoscope adapted for directly visualizing the cords. Endoscopic visualization is both difficult and time consuming and frequently impractical in any emergency setting. Once the patient is stabilized, radiographic verification can further confirm intubation. When endoscopic visualization equipment is not available for confirmation that the endotracheal tube is correctly positioned and radiography is impractical, auscultation of the bilateral lung fields, especially over the lateral axillary regions, may be employed. Auscultation of the properly intubated patient should produce equal breath sounds over both fields. Stethoscope auscultation over the epigastrium can be employed to ensure that the esophagus has not been intubated. The absence of air sounds over the epigastrium on ventilation indicates placement of the tube within the esophagus has not occurred. Disposable end-tidal $CO_2$ detectors disposed in-line with the endotracheal tube airway have also been employed to detect or verify the position of the endotracheal tube within the airway of the patient. The $CO_2$ detector comprises an element which changes color in response to the presence of $CO_2$. Such a $CO_2$ detector device is described, for example, in U.S. Pat. Nos. 4,879,999, 4,994,117 and 5,124,129.

Following intubation the endotracheal tube cuff is inflated. A syringe may then be used to aspirate air from the patient's lungs through the endotracheal tube. A syringe aspiration device consists of a 60 ml syringe connected to a straight ventilator circuit adapter. Aspiration of about 60 ml of air from the endotracheal tube is then attempted by retracting the plunger of the syringe. Proper intubation of the trachea is assumed if the syringe plunger can be easily retracted without resistance or rebound. If aspiration is met with resistance, or if the plunger rebounds, esophageal intubation may be assumed to have occurred. U.S. Pat. No. 5,309,903 to Long describes a syringe and means for connecting the syringe to an airway for delivering a surfactant to an intubated patient. A device similar to the arrangement shown for the Long apparatus (without the medicament) may be conveniently used for aspiration verification of proper intubation.

Many devices have been considered which utilize sound generated by a patient's breathing to either monitor the patient's breathing or to verify the correct placement of an endotracheal tube within the patient's airway. A representative sonant device is disclosed in U.S. Pat. No. 5,331,967 to Akerson which describes an acoustic resonance cavity which may be acoustically coupled to the airway of a patient. The acoustic cavity has a resonance frequency which is determined experimentally. Upon insertion of an eudotracheal tube within a patient's airway, the acoustic resonance cavity is coupled to the airway of the patient by means of a endotracheal tube adapter. The resonance frequency (or the amplitude of the acoustic resonance standing wave) within the chamber changes in a predetermined way thereby indicating acoustic connection between the airway of the patient and the acoustic cavity and verifying intubation.

U.S. Pat. No. 4,773,412 to Bloom discloses a device which may be attached to a tracheostomy tube for generating sound, which sound may be modulated by the patient for effecting speech. Other devices which employ sound for either monitoring respiration or for verifying position of an endotrachael tube following intubation are presented in U.S. Pat. Nos. 5,056,514; 4,949,716; 5,083,560, and 2,376,971. The sonant devices described in the foregoing patents each employ sound. The sound may be caused by the passage of air through the patient's airway or a synthetic audio signal or "sound" is detected by means placed within the airway. These sonant methods of monitoring air passage are in many instances adequate for verifying tube placement but are generally expensive and do not provide information regarding the condition of the lung itself. Such devices are not suitable or generally operable for determining the presence of a pneumothorax or a hemothorax.

While the foregoing devices each provide certain advantages in determining the patency of an airway or verifying the position of an endotrachael tube within a patient, none of the above prior art devices provide additional information on the condition of the lungs themselves. Further, the above intubation verification devices such as $CO_2$ detectors and endotracheal endoscopes, are expensive and, in the case of endoscopes, require extensive training in order to be applied. The aspirator syringe method for verifying the correct position of a endotracheal tube within an airway appears to be both simple to use and accurate for verifying the position of the endotrachael tube within the airway. It would be particularly advantageous to provide an in-line device for incorporation into an adjunctive airway of an intubated patient presenting both the ability to verify the correct position of an endotracheal tube and provide additional information regarding the condition of the patients lungs.

SUMMARY OF THE INVENTION

It is a first object of the invention to provide a device for verifying the position of an endotracheal tube within the airway of an intubated patient.

It is another object of the invention to provide a device which, in addition to determining the placement of an endotracheal tube within a patient, can provide information regarding the condition of the patient's pleural cavity.

It is still another object of the invention to provide a device and a method for using the device to detect the presence of a pneumothorax or a hemothorax in an intubated patient.

It is still another object of the invention to provide a device operable for providing the foregoing information which is compact, disposable and requires no special training to use.

It is yet a further object of the invention to provide a device for determining the patency of an intubated patient's airway by osculation and which may be used in a noisy environment.

The features of the invention believed to be novel are set forth with particularity in the appended claims. However, the invention itself, both as to organization and method of operation, together with further objects and advantages thereof may best be understood by reference to the following description taken in conjunction with the accompanying drawings in which:

BRIEF DESCRIPTION OF THE DRAWINGS

FIG. 1 is a plan view of a patient showing the distal end of an endotracheal tube placed within the patient's trachea and the proximal end of the endotracheal tube connected to the indicator device of the present invention.

FIG. 2a is a plan view of the external, non-invasive portion of a ventilating airway showing the position of the indicator device in the ventilating airway with respect to the ambubag and the endotracheal tube.

FIG. 2b is an elevational cross-sectional view of the indicator device of FIG. 2a.

DESCRIPTION OF THE PREFERRED EMBODIMENTS

Figure 3:
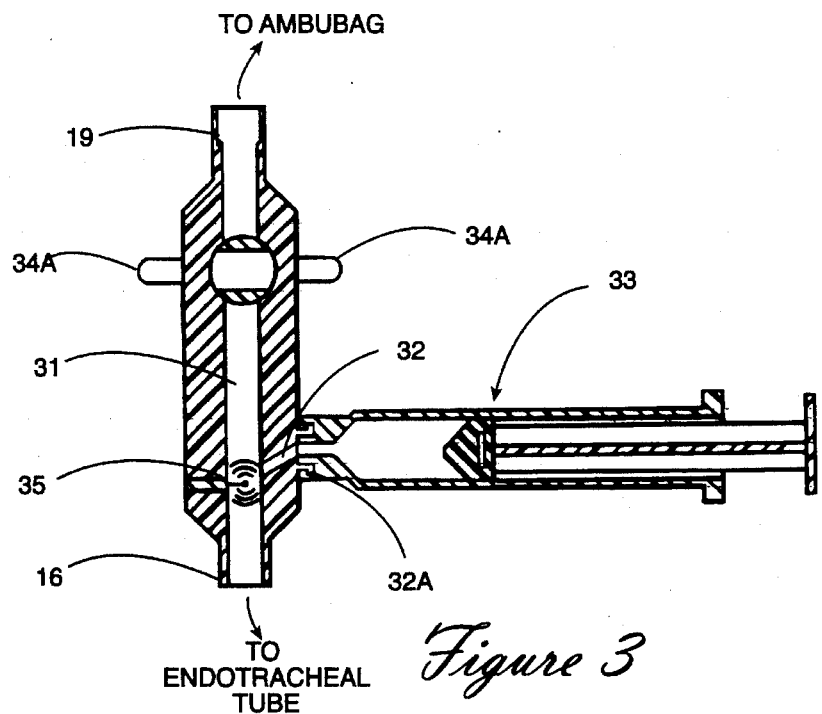
FIG. 3 is a vertical cross-sectional view of an embodiment of the indicator device of the present invention employing a syringe to verify intubation and showing the lumen valve closed and the audible vibration (signal) generator operating (optional) during syringe aspiration of the patient's airway.
Figure 4:
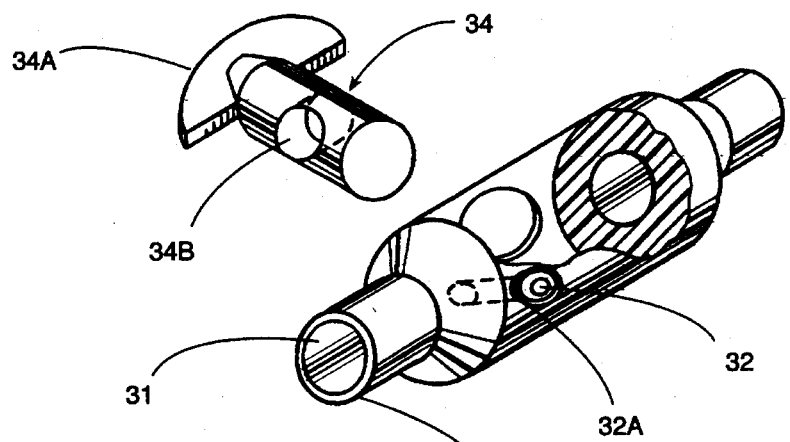
FIG. 4 is a partially cutaway perspective view of the indicator device of the present invention showing a portion of the outer casing broken away to illustrate the internal construction.
Figure 5:
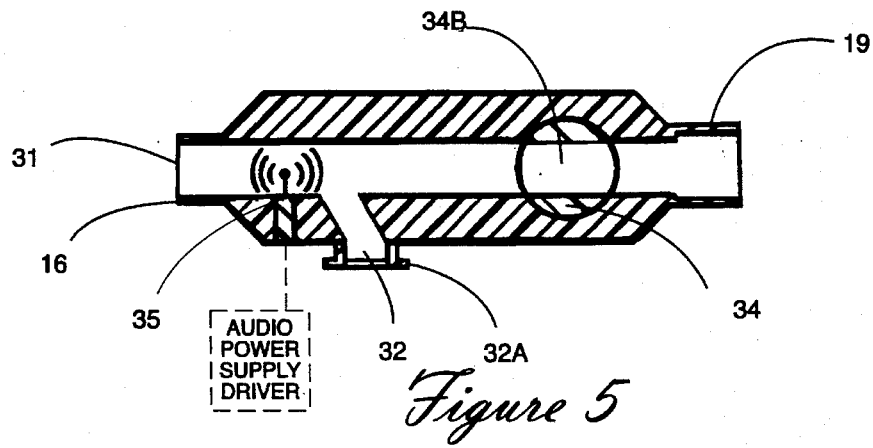
FIG. 5 is a longitudinal cross-sectional view of the embodiment of the device of FIG. 3 wherein the aspiration syringe is disconnected from the device and the lumen valve is open and the audible vibration generator is operating.

Turning first to FIG. 1, the indicator device, indicated at arrow 10 (alternatively referred to herein as "the device" or "the device of the present invention," is shown in combination with the prior art components of an adjunctive airway comprising an invasive endotracheal tube 11 having a distal end 12. The distal end 12 of the endotracheal tube 11 is shown inserted within the trachea 13 of a patient 14. A balloon-like inflatable cuff 15 on the distal end 12 of the endotracheal tube 11 is inflated by means of a syringe (not shown) when the distal end 12 of the tube is properly positioned within the trachea. The proximal end 17 of the endotracheal tube 11 has an adapter 18 thereon which may comprise a male projection or a female receptacle which releasably engages a first mating attachment means affixed to the distal end 16 of the device 10. The proximal end 19 of device 10 has second attachment means thereon operable for releasably engaging a mating fitting on an ambubag (not shown in FIG. 1 ) which ambubag 22 (FIG. 2), in turn, is normally attached to a source of ventilating gas such as an air or oxygen in a manner well known in the art.

In FIG. 2, the device 10 in accordance with the present invention is shown in cooperative and positional relationship to the other components of the ad junctive airway. The ambubag 22 has a vent tube 23 having a one-way valve 24 which permits the flow of ventilating gas from the ambubag 22 to flow through the vent tube 23 in the direction of the endotracheal tube 11. The one-way valve 24 prevents exhaled gas from the patient from entering the ambubag 22. A second, one-way escape valve, not shown, is normally provided on the adjunctive airway between the ambubag and the endotracheal tube to provide means for the patient's exhaled air to be vented from the airway.

With reference now to FIG. 3, the device 10 has a airway lumen 31 which is coextensive with the device; extending from the proximal end 19 to the distal end 16. The airway lumen 31 is dimensioned to permit sufficient gas to flow to the patient to enable external control and management of the patient's ventilation. In a preferred embodiment, the lumen 31 is bifurcated within the device. An aspirator lumen 32 provides fluid communication between the airway lumen 31 and syringe connection means 32a operable for attaching a syringe 33 thereto. The syringe 33 is preferably a 60 ml or greater syringe and provides means for aspirating air from the patient's lungs through the endotracheal tube to verify the position of the endotracheal tube within the airway of the patient. In the event that plunger resistance is met during syringe aspiration, it can be assumed that the endotracheal tube has entered the esophagus and immediate corrective action should be performed. A stopcock 34 permits the ambubag 22 to be isolated from the airway lumen 31 of the device 10. The syringe 33 can then be employed to aspirate air only from the patient's airway. After verification of proper intubation, the stopcock 34 is opened and the syringe 33 may either be left in place or removed from the device if stopcock means (not shown) is interposed between the syringe 33 and the syringe connection port 32 of the device.

After the syringe 33 has been employed to verify the position of the endotrachael tube within the airway of the patient, the condition of the patient's lungs may be examined by means of a stethoscope placed on the chest of the patient. The device 10 has an audible sound generating portion 35. The sound generating portion may be either a pneumatically responsive device such as a split reed or whistle or a "duckbill" which vibrates at an audible frequency in response to the passage of air thereby, or it may be a electrically driven piezo or electromagnetic audible sound generating device. The audible sound source is preferably an externally powered audible sound generator which produces audible sound vibrations at one or more frequencies within the adjunctive airway which are readily transmitted through the adjunctive and patient's airway to the patient's lungs. Osculation of the sound at the patient's chest provides information regarding the condition of the lungs. A collapsed lung will provide an attenuated sound amplitude at the chest wall overlying the collapsed lung. Further, bilateral similarity in the sound intensity at the chest wall indicates operable lungs. The present device provides means for both determining: (a) whether an intubated patient's airway is patent by providing means for connecting an aspiration syringe to the patient's airway; and (b) non-invasive means (an audible signal generator) for determining the presence of a hemothorax or a pneumothorax. In a noisy, emergency room environment, detecting breathing sounds by means of a stethoscope is difficult. The present device provides means for generating a audible vibration at a preferred frequency and coupling the audible Vibration into the adjunctive airway, the audible vibration thereafter to be conducted through the (intubated) patient's airway into the lungs where the vibration is transmitted to the pleural cavity and the chest wall where it can be non-invasively monitored. By generating only preferred audible frequencies such as 100–200 Hz and/or 10,000–20,000 Hz which are more easily detected in the presence of "white" noise than the midrange enables the attending practitioner to more easily distinguish the sound at the chest wall from background noise.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A method for determining a presence of an impaired lung within an intubated patient comprising the steps of:

(a) inserting an endotracheal tube into the patient's airway;

(b) presenting a sound generator operable for generating an audible sound;

(c) attaching a means for vibrationally coupling the audible sound generated by the sound generator into the patient's airway to the endotracheal tube;

(d) activating the sound generator thereby causing production of an audible sound; and (e) measuring intensity of the audible sound conducted to the chest wall, the intensity of the sound providing a measure of the impairment.

2. An indicator device adapted for incorporation within an adjuctive airway and disposed between a gas ventilating apparatus with a distal end and an endotracheal tube, and for use with a syringe, the endotracheal tube having a distal end inserted within a patient's airway and a proximal end extending out of the patient's airway, wherein the indicator device comprises:

a body portion with distal and proximal ends joined by an air conducting lumen therebetween, said distal end of said device having means thereon for air tight connection to the proximal end of the endotracheal tube, said proximal end of said device having means thereon for air tight connection to the distal end of the gas ventilating apparatus;

an aspirator lumen which connects at a first end with said air conducting lumen and which has a syringe attachment means at a second end; and a stopcock disposed in said air conducting lumen between said proximal end of said body portion and an intersecting point of said aspirator lumen and said air conducting lumen for accurately determining proper intubation of the trachea.

3. The indicator device of claim 2 further comprising a vibrating element disposed within said body portion, at least a portion of said vibrating element being in vibrational communication with said air conducting lumen.

4. The indicator device of claim 3 wherein said vibrating element is selected from one of a pneumatically responsive device and an electrically driven audible sound generating device.

5. A device for use in combination with an endotracheal tube, a gas ventilating device, and a syringe, said device adapted for verifying the correct placement of an endotracheal tube within an intubated animal's airway and for detecting the presence of a collapsed lung, the device comprising:

a generally tubular body portion with an open proximal end and an open distal end traversed by an air conducting lumen, said proximal end having connection means thereon operable for forming an air tight connection with the endotracheal tube, said distal end having connection means thereon operable for forming an air tight connection with the gas ventilating device;

an aspirator lumen which connects at a first end with said air conducting lumen and which has a syringe attachment means at a second end adapted to connect to a syringe;

a stopcock disposed in said air conducting lumen between said proximal end of said body portion and an intersecting point of said aspirator lumen and said air conducting lumen; and a vibrating element disposed within said device, at least a potion of said vibrating element being in vibrational communication with said air conducting lumen for accurately determining proper intubation of the trachea.

6. The indicator device of claim 5 wherein said vibrating element is selected from one of a pneumatically responsive device and an electrically driven audible sound generating device.

* * * * *